United States Patent

Grundei et al.

Patent Number: 5,766,263
Date of Patent: Jun. 16, 1998

[54] FEMUR ENDOPROSTHESIS FOR ARTIFICIAL HIP JOINT

[75] Inventors: Hans Grundei, Lübeck; Jörg Scholz, Berlin, both of Germany

[73] Assignee: Eska Implants GmbH & Co., Lübeck, Germany

[21] Appl. No.: 783,476

[22] Filed: Jan. 14, 1997

[30] Foreign Application Priority Data

Jan. 16, 1996 [DE] Germany ............... 196 01 340.2

[51] Int. Cl.$^6$ ........................................ A61F 2/36
[52] U.S. Cl. ............................................. 623/23
[58] Field of Search ..................... 623/18, 22, 23

[56] References Cited

U.S. PATENT DOCUMENTS

| | | | |
|---|---|---|---|
| 2,682,265 | 6/1954 | Collison | 623/23 |
| 4,129,903 | 12/1978 | Huggler | 623/23 |
| 4,795,473 | 1/1989 | Grimes | 623/23 |
| 4,938,772 | 7/1990 | Frey et al. | 623/23 |
| 4,976,740 | 12/1990 | Kleiner | 623/23 |
| 5,178,201 | 1/1993 | Ahlers | 623/23 |
| 5,433,750 | 7/1995 | Gradinger et al. | 623/16 |

FOREIGN PATENT DOCUMENTS

| | | |
|---|---|---|
| 0 099 167 A1 | 1/1984 | European Pat. Off. |
| 0 230 006 A1 | 7/1987 | European Pat. Off. |
| 0 561 263 A1 | 9/1993 | European Pat. Off. |
| 2 617 706 | 1/1989 | France ............... 623/23 |
| 2 626 169 A1 | 7/1989 | France |
| 2 674 122 A1 | 9/1992 | France |
| 30 17 953 A1 | 2/1981 | Germany |
| 27 24 234 C2 | 1/1986 | Germany |
| 36 07 824 A1 | 9/1987 | Germany |
| 2 166 359 | 5/1986 | United Kingdom ............. 623/23 |
| 2 166 359 A | 5/1986 | United Kingdom |
| WO 89/11837 | 12/1989 | WIPO |
| WO 93/01769 | 2/1993 | WIPO |

*Primary Examiner*—Mary Beth Jones
*Attorney, Agent, or Firm*—Panitch Schwarze Jacobs & Nadel, P.C.

[57] ABSTRACT

A femur endoprosthesis for an artificial hip joint includes (a) a shell (1) which can be implanted without cement in the upper region of a femur below the greater trochanter, the proximal end (8) of the shell being connectable with an adapter (2) for accommodating an artificial spherical joint part (20), wherein the exterior of the shell is at least partially covered with an open-meshed three-dimensional spatial lattice structure (9), and (b) a draw plate (3) in which a draw-in screw (4) can be fastened, which can be inserted in the interior of the shell through a through bore (5) in its distal end (6), and which can be screwed in with a thread (7) provided therein.

11 Claims, 3 Drawing Sheets

FEMUR ENDOPROSTHESIS FOR ARTIFICIAL HIP JOINT

BACKGROUND OF THE INVENTION

The invention concerns a femur endoprosthesis for an artificial hip joint.

Two treatment possibilities have proven themselves during recent decades for treatment of a destroyed femur head from which considerable sensations of pain and serious functional restrictions of the joint result:

First, it is possible to provide the patient with an orthotic device, that is with an external support apparatus. In addition to the fact that this therapeutic possibility is completely unacceptable from a cosmetic point of view, it is also less than optimal from the perspective of therapeutic technology.

A further, more widely accepted possibility is to provide the patient with an endoprosthesis, namely a hip stem endoprosthesis, in connection with which a stem is installed in the previously excavated bone marrow area of the femur and is there fixed without cement or with the use of a cement. Such an endoprosthesis then offers the possibility of connection on the proximal side with an artificial spherical joint part.

It is precisely the latter possibility which is strongly represented in patent literature. At this point, reference is made to DE-U-94 12 408 only as an example.

There are some approaches which are quite promising with respect to long-term stability in the patient's body among the one or others of the hip stem endoprostheses proposed in patent literature. Sooner or later, however, for example after 10 to 15 years, subjection of the endoprosthesis to wear and tear is observed which leads to the necessity of a revision intervention to remove the implanted endoprosthesis and replace it by a new one. This is certainly not wholly without problems, as a considerable portion of the natural bone material is removed with the initial implantation by the resection and clearing of the bone marrow area. The material once removed is then possibly absent with a revision intervention. This then especially has an effect when the patients are relatively young, with whom one must assume from the beginning that they will be subjected to at least one revision intervention in the course of their lives.

An endoprosthesis which manages with a more minor resection of natural bone material than the familiar hip stem endoprostheses is known from DE-27 24 234C2. The prosthetic element described there is implanted in the upper region of a femur but below the lesser trochanter without a stem extending into the bone marrow area. This prosthesis, which is also designated as a thrust washer endoprosthesis, basically reaches over the cortex of the femur subjected to resection in the area of the removed hip joint head with a proximal fastening plate. It is braced with a fastening plate which lies laterally on the femur in such a manner that all mechanical forces between the endoprosthesis and the femur are directly introduced into the cortical layer of the femur, by means of which a mechanical strain on the spongiosa, which is felt to be impermissible, should be avoided. Only a small amount of bone cement is necessary for fixing the thrust washer in the proximal region.

As explained, underlying the philosophy of this endoprosthesis is the assumption that the spongiosa of the femur should be subjected to as little strain as possible. This is achieved at the expense of an extreme stress upon the cortex of the femur, since namely all forces are unloaded on it and introduced into it. This in no way corresponds to natural stress conditions according to current knowledge.

WO 89/11837 moreover shows a endoprosthesis which operates quite similarly in which the function of the proximal fastening plate is undertaken, in accordance with the previously mentioned publication, by the specially constructed hip joint head, which is provided with an interior recess on which the femur stump, which has been subjected to resection, is installed in the interior under application of pressure.

Two prostheses in connection with which the main burden is apparently to be assumed by the spongiosa of the femur bone have become known from FR 26 26 169 A1 and FR 26 74 122 A1. In the first named publication of the two, there is provided a thread bolt, which has a proximal plug-in cone, for screwing into the spongiosa. This may lead to severe instability problems within a very short time. With the second named publication of the two, a plate bearing a plug-in cone is fastened by means of a series of bone screws, whereby the bone screws reach into the spongiosa. Serious stability questions also arise from this, as the spongiosa by its nature can only be subjected to slight point stress in comparison with the cortex of the femur bone.

BRIEF SUMMARY OF THE INVENTION

Against this background, it is therefore the objective of the present invention to provide a femur endoprosthesis for an artificial hip joint which is considerably better adapted than the aforementioned prostheses to natural conditions with respect to the introduction of force into the femur, where resections of natural bone material become necessary only to a small extent. This objective is accomplished in that the femur endoprosthesis has:

A shell which can be implanted without cement in the upper region of a femur below the greater trochanter, the proximal end of the shell being connectable with an adapter for accommodating an artificial spherical part of a joint, whereby the exterior of the shell is at least partially covered with an open-meshed three-dimensional spatial lattice structure, as well as A draw plate on which a draw-in screw can be fastened, which can be placed in the interior of the shell through a through bore in its distal end, and which can be screwed in with a thread provided therein.

In contrast with the thrust washer endoprosthesis described above, the forces of stress are not introduced into the femur cortex, but directly into the spongiosa in the interior of the femur, after bone trabeculae have grown through the open-meshed three-dimensional spatial lattice structure on the shell exterior during the healing phase. Thus, precisely the path is described with the endoprosthesis of the invention which has been viewed as disadvantageous in DE-27 24 234, namely putting stress upon the spongiosa. After the healing phase, the shell of the endoprosthesis acts dynamically in imitating natural conditions on the basis of its quasi suspension on numerous bone trabeculae. That is, it can definitely reconstruct evasive movements depending upon the stresses in question, and can execute compensatory movements. This type of fixation of an endoprosthesis corresponds to recent knowledge from surgery, namely that in a tubular bone, the main stresses are absorbed not by the cortex, but rather by the spongiosa. No pressure loading of the cortex takes place with the endoprosthesis of the invention.

As a preparation for the implantation, the destroyed head of the femur is first removed by a subcapital resection, and to be sure basically orthograde to the axis of the femur neck. Driving into the neck of the femur then takes place using a milling tool which basically has the same exterior contour as the shell to be implanted, and a corresponding boring or excavation of the spongiosa of the femur is produced. The shell can then be implanted in the milled out area in the neck of the femur. Installing the draw plate mentioned above (which can be screwed into the interior of the shell using a draw-in screw) to the femur from the outside is intended to fasten the shell laterally. For this purpose, it is necessary to bore into the cortex laterally so that the draw-in screw can be guided through the cortex into the interior of the shell in order to be screwed in there. The draw plate with the draw-in screw comprises a basically familiar tension flange system.

The adapter which is to be connected with the proximal end of the shell can assume any desired suitable shape. Generally, it is necessary to take care that no effects arise in connection with the thrust washer as they are known from the aforementioned DE-A-27 24 234. The shell should advantageously have an ovalshaped configuration in cross section. A rotational stability of the shell in the spongiosa is thereby attained in advance.

Moreover, constructing the shell in such a manner that it tapers conically from its proximal to its distal end is preferred. First, this corresponds more or less to the conical configuration of the neck of the femur, thus representing an anatomical adaptation. Second, the distribution of force becomes more suitable during the healing phase by surface pressure as with an osteosynthesis, if the shell is braced with the draw-in screw and set under load, than if the shell is, for example, constructed cylindrically.

The spatial lattice structure on the shell exterior must not be of homogeneous reticulation. It is rather provided in accordance with an advantageous development that for the spatial lattice structure be constructed with a coarse mesh with mesh widths between 3 and 6 mm on its exterior which points in a cranial and caudal direction (thus upward and downward). This corresponds to the main directions of load in the natural spongiosa bed in the femur and the trajectories of the spongiosa tissue of the natural implant bearing in the femur.

Constructing the spatial lattice structure with a fine mesh with mesh widths between 1 and 2.5 mm in a ventral and dorsal direction on the shell exterior is advantageously provided as a further anatomical adaptation. The oval shape of the cross section of the shell already mentioned automatically results in this case when the spatial lattice structure is constructed with two different mesh sizes on the shell exterior. In this case, the larger main axis of the oval would be sought in areas in which the coarse meshed spatial lattice structure is arranged, while the smaller secondary axis, on the other hand, would be sought in connection with the smaller mesh sizes.

It is provided in an especially preferred construction that the adapter for the spherical joint part is basically configured as a double plug cone with a flange running around both cone bases, wherein in the proximal area a conical plug socket is provided, constructed conforming to the one plug-cone. A conical compression joint can thus also be constructed according to known principles between the one plug cone and the plug shell in the socket, while on the other hand, the other plug cone works together with a plug socket in an artificial condyle.

The following should be noted in this connection: The flange running around on both cone bases does not serve for emplacement on the resection surface, as is the case for example, with the proximal thrust washer in accordance with DE-27 24 234C2. Ideally, a gap of about 1 mm in width is located between the resection surface and the side of the flange facing this surface, after production of the conical compression joint with the implanted shell. In the course of time, this is grown through with bone trabeculae after implantation, if the flange is covered with an openmeshed three-dimensional spatial lattice structure on its outward facing surfaces. This arrestation merely serves to anchor the adapter, not to introduce load forces into the femur cortex. As an alternative, fastening using screws would also be conceivable.

In the event a revision intervention becomes necessary, the blade of a saw fits into the gap mentioned above with which the bone trabeculae between adapter, flange and resection surface can simply be separated, so that the adapter can simply be withdrawn from the shell using an extraction tool.

The adapter can moreover be safeguarded in its conical compression fit by a further advantageous measure wherein a blind bore is provided with internal threads in the plug cone of the adapter facing the shell, with which the end of the draw-in screw provided with a corresponding thread section can be screwed in for arrestation. In this case, the draw-in screw thus reaches through the interior of the shell far beyond the thread, with which the draw plate can be screwed together with the shell by means of the draw-in screw, namely far into the region of the proximal plug shell. The plug cone of the adapter is thus in this case generally drawn into the conical collet of the shell in the femur using the draw-in screw and there anchored immovably.

In order that loosening does not occur after producing a connection between shell and draw plate outside on the femur cortex when the connection between the adapter and the shell is generated, the thread section at the end of the draw-in screw preferably has a different pitch than the thread in the shell interior. A self counteraction is attained by this means which precisely prevents a loosening of the connection first produced.

In accordance with a still further advantageous embodiment of the femur endoprosthesis, it is provided that the surfaces of the draw plate facing the femur are likewise covered with an open-meshed three-dimensional spatial lattice structure. In this way, there occurs a further anchoring of the implant against micro-motions under loads. Theoretically, the draw plate could indeed be dispensed with after a complete settling of the shell in the spongiosa area of the femur, as this type of fixation leads to an extremely intimate connection between implant and the surrounding bone. Considerations with regard to long-term fixation and with respect to avoiding an unnecessary risk can nonetheless make it appear desirable to provide this additional safety measure in the draw plate.

A further safety measure with regard to the position of the draw plate on the lateral cortex of the femur is then advantageously present if the draw plate is provided with at least one abutment in the form of a peg pointing in the direction of the femur, which basically forms the same angle $\alpha$ with the draw plate as the main axis of the shell with the draw plate, whereby as the axis of the draw plate its main axis is to be understood. The abutment acts so as to inhibit rotation. At the same time, any bending moments can be unloaded.

BRIEF DESCRIPTION OF THE SEVERAL VIEWS OF THE DRAWING

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings.

DETAILED DESCRIPTION OF THE INVENTION

Figure 1:
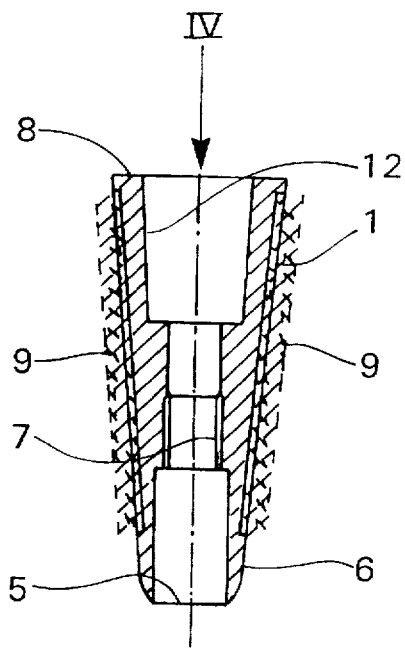
FIG. 1 is a sectional view of a shell of the endoprosthesis to be implanted in the femur.

The same parts are provided with the same reference designations below. The shell 1 of the endoprosthesis of the invention is presented in FIG. 1. The shell has a proximal end 8 and a distal end 6. In the embodiment presented, the shell runs conically narrowing from its proximal end 8 to its distal end 6, which brings about the desired actions with respect to distribution of force. The shell 1 represented in section is covered on its exterior surface with an open-meshed three-dimensional spatial lattice structure 9 of relatively coarser mesh width (3 to 6 mm), and to be sure on the shell exterior sides which face caudally and cranially after implantation in the femur. This corresponds in anatomical adaptation approximately to the sizes of the natural bone trabeculae in the neck of the femur.

Figure 4:
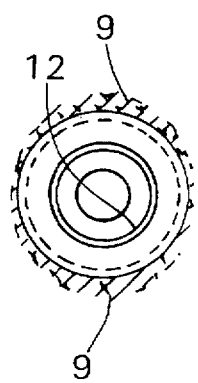
FIG. 4 is a view of the proximal end of the shell in the direction of the arrow IV in FIG. 1.

An open-meshed three-dimensional spatial lattice structure 9 is to be sure likewise provided on the shell exterior sides facing ventrally and dorsally (FIG. 4), but with basically smaller mesh width as is presented schematically in FIG. 4. The mesh width amount to about 1 to 2.5 mm.

A through bore 5 is provided in the distal end of the shell 1 which incorporates an internal thread 7 in the direction of the proximal end 8 of the shell 1. This transitions into a cylindrical boring which finally terminates in a conical collet 12 at the proximal end 8.

Figure 2:
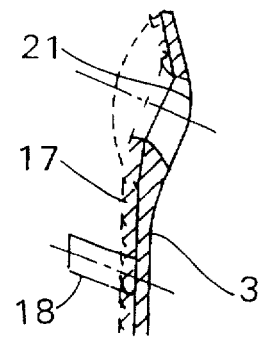
FIG. 2 is a sectional view of the draw plate of the endoprosthesis.

A further important component of the endoprosthesis is the draw plate 3, as it is depicted in an exemplary embodiment in FIG. 2 in cross-sectional view. It basically comprises a plate-shaped element which has an aperture 21 for guiding a draw-in screw, as will be explained in greater detail below.

The draw plate has an open-meshed three-dimensional spatial lattice structure on its surface facing toward the femur, through which bone trabeculae grow proceeding from the cortex of the femur, in order to achieve a positional fixation of the draw plate 3, and thus also of the shell 1 connected with it after implantation.

As is apparent, the draw plate 3 has an abutment in the form of a peg 18 in the direction of the femur, which is here inclined in the same axis as the main axis of the shell 1 toward the draw plate 3. In this way, a particular stability with respect to any possible bending moments applied is attained.

Figure 3:
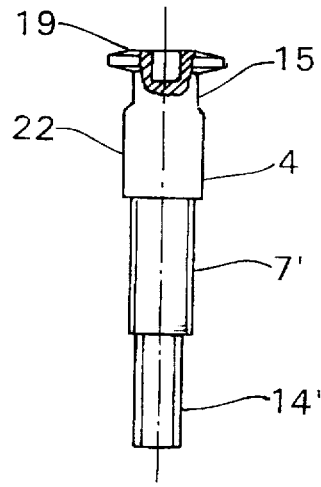
FIG. 3 is a view of the draw-in screw.

FIG. 3 shows a view of the draw-in screw 4. Proceeding from its head 19, this has four sections. First of all, a cylindrical section 15 with a reduced diameter, in comparison with the adjoining cylindrical section 22, is connected to the head 19. A thread section 7' in turn follows upon this, to which a further thread section 14' is connected. This thread section 7' works together with the internal thread 7 in the shell 1, namely when the draw-in screw 4 is guided through the draw plate 3 and the boring in the femur cortex through the through bore 5 into the shell 1. The draw-in screw 4, so to speak, draws the shell laterally into its implantation position by means of the draw plate 3. The reduced diameter section 15 serves for fine adjustment of the position of the draw-in screw 4 in the draw plate in its aperture 21.

Figure 5:
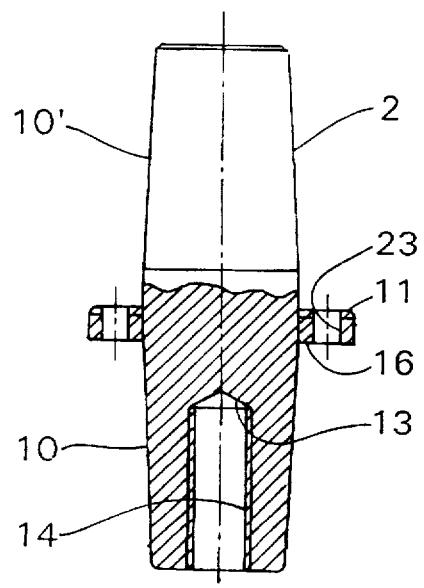
FIG. 5 is a partial sectional view of the adapter for accommodating an artificial spherical joint part.

The distal thread section 14' of the draw-in screw 4 works together with the adapter 2, as it is presented partially in section in FIG. 5, for example. The adapter 2 presently consists of two plug cones 10 and 10' which project jut away from each other. The plug cone 10 is provided for insertion in plug socket 12 and there to remain under the action of the conical compression joint. A blind bore 13 with an internal thread 14 is provided in plug cone to secure the position further. The thread section 14' of the draw-in screw 4 is screwed in with this internal thread 14.

An artificial spherical joint part can be connected with the other plug cone 10' in the usual manner, likewise under the action of a conical compression joint to be produced between the cone 10' and a plug socket in the spherical joint part.

An annular flange 11 is constructed in the area of the bases of the cones 10 and 10' of the adapter 2'. This flange does not serve (as already remarked above) to form an unloading on the resection surface of the femur. The flange merely serves to guard against rotation. For this purpose, some peripheral borings 23 are provided in the flange 11, through which suitable means of attachment (not depicted) can be placed in order to implement a rotational security. For example, small screws could be guided into the femur could be guided through the borings 23. As an alternative to this, or in addition to this attachment possibility, it is provided that the outward facing surfaces of the flange 11 are covered with an open-meshed three-dimensional spatial lattice structure 16. Following implantation of the endoprosthesis, bone trabeculae will grow from the resection surface of the femur into these spatial structures or grow through them and thus lead to a rotational stability.

Preferably, the implantation of the endoprosthesis takes place so that a gap of, for example, 1 mm remains free between the resection surface and the flange 11. This gap can be overcome by the bone trabeculae without difficulty, but nonetheless, it can easily be separated again by inserting a saw blade in the gap during a revision intervention.

Figure 6:
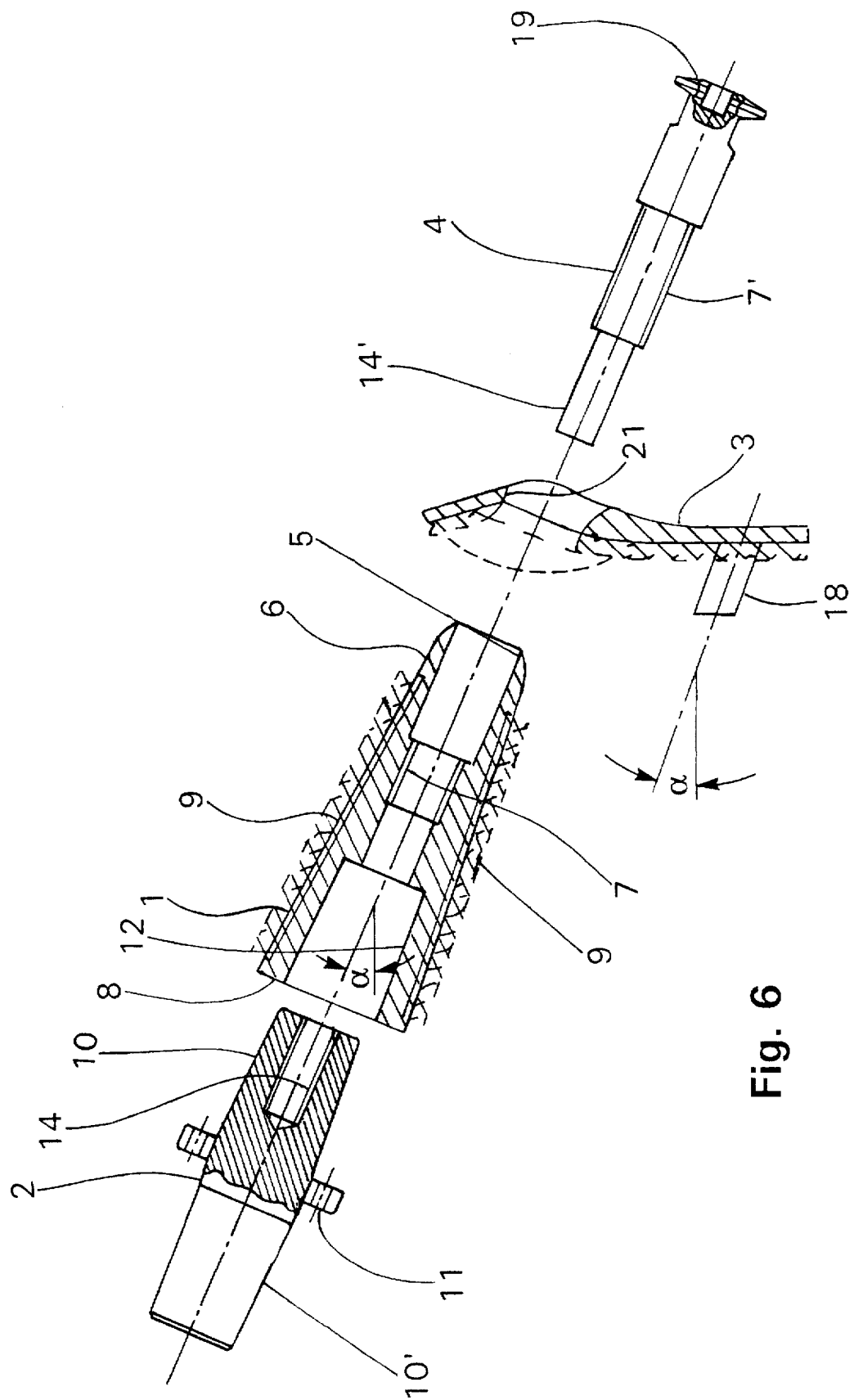
FIG. 6 is a schematic representation of the components of the endoprosthesis from FIGS. 1 to 5 with relative positioning corresponding to the relative position in the implantation.

The effect of the joint operation of the previously described components of the endoprosthesis appears schematically in FIG. 6.

During implantation, the lateral cortex of the femur (not depicted) is situated between the draw plate 3 and the shell 1. The draw-in screw 4 is guided through the aperture 21 in the draw plate 3 and through the boring in the cortex into the shell 1. After that the thread section 7' of the draw-in screw draw-in screw 4 is screwed into the shell 1 with the internal thread 7, whereby the shell 1 is then drawn toward the exterior (laterally). After this, the adapter 2 can be applied to the shell 1 while inserting the plug cone 10 of the adapter 2 into the plug socket 12 in the shell 1. This takes place in the case depicted by screwing in the adapter, whereby the thread section 14' of the draw-in screw 4 is engaged by the internal thread 14 of plug cone 10.

A rotational stability of the shell 1 is attained from the beginning owing to the oval cross section shape, which in the present case results from covering the outer surface of the shell 1 with open-meshed three-dimensional spatial lattice structures with different mesh sizes, as described above.

Figure 7:
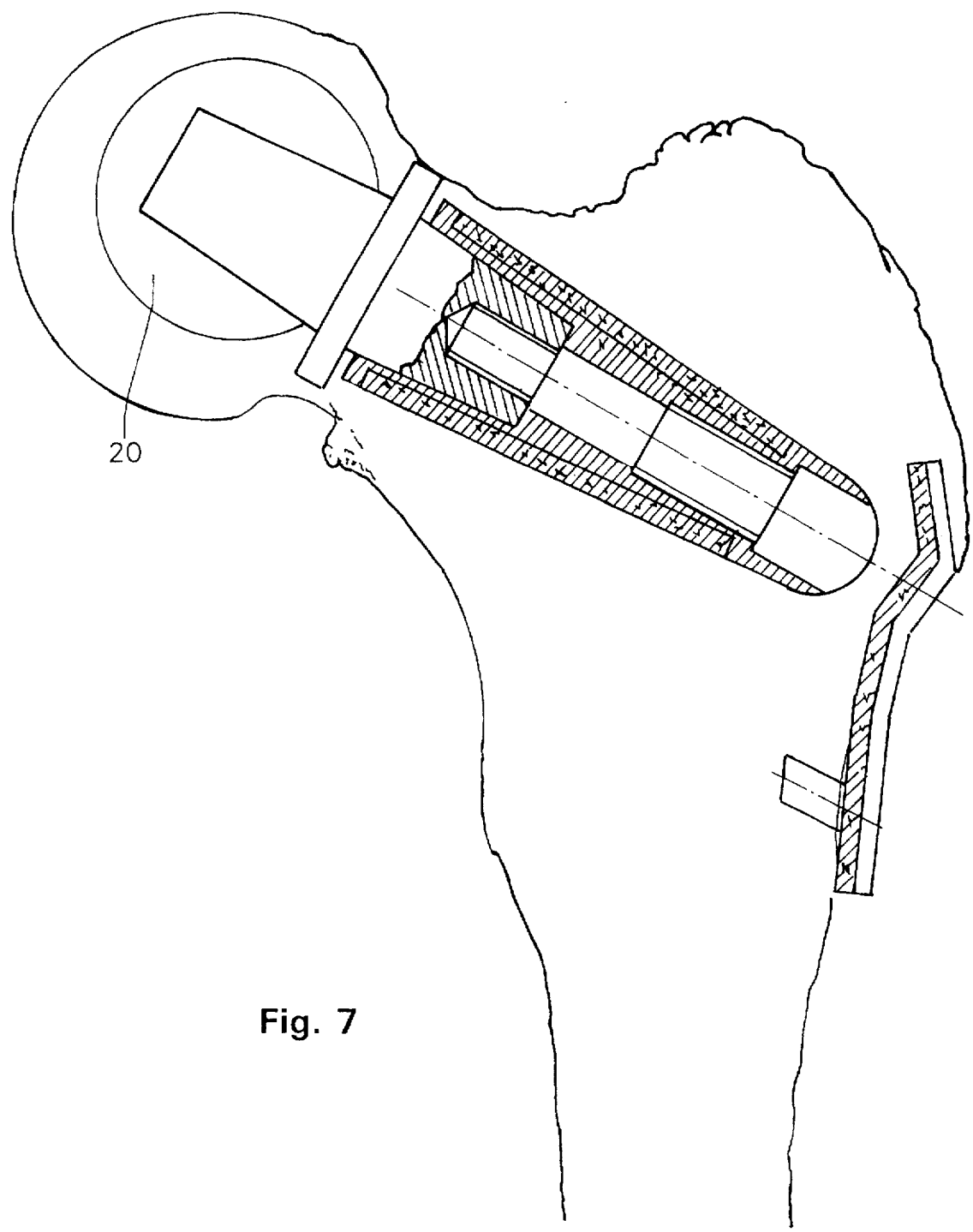
FIG. 7 is a schematic representation of the implantation position of the endoprosthesis in the neck of a femur.

Finally, it is necessary to refer to briefly FIG. 7, from which the position of the endoprosthesis in situ becomes apparent. Depicted in addition is an artificial spherical joint part 20 which acts in conjunction with an artificial joint socket in order to yield an artificial hip joint. The representation in FIG. 7 only serves to assist in visualization.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A femur endoprosthesis for an artificial hip joint, comprising:

a shell (1) which can be implanted without cement in an upper region of a femur below its greater trochanter, a proximal end (8) of the shell being connected with an adapter (2) for accommodating an artificial spherical joint part (20), wherein an exterior of the shell is at least partially covered with an open-meshed three-dimensional spatial lattice structure (9), and a draw plate (3) through which a draw-in screw (4) is fastened, the draw-in screw being inserted in an interior of the shell through a through bore (5) in a distal end (6) of the shell and being screwed directly into the shell interior with a thread (7) provided in the shell.

2. The femur endoprosthesis according to claim 1, wherein the shell (1) is constructed as tapering conically from its proximal end (8) to its distal end (6).

3. The femur endoprosthesis according to claim 1, wherein the spatial lattice structure (9) is constructed with a coarse mesh having mesh widths between 3 and 6 mm on shell exterior sides facing in caudal and cranial directions.

4. Femur endoprosthesis according to claim 1, wherein the spatial lattice structure (9) is constructed with a fine mesh having mesh widths between 1 and 2.5 mm in ventral and dorsal directions on the shell exterior.

5. The femur endoprosthesis according to claim 1, wherein the adapter (2) for a spherical joint part is constructed essentially as a double plug cone (10, 10') having an annular rotating flange (11) on bases of the two cones and wherein a correspondingly constructed conical plug socket (12) is provided in the proximal area of the shell (1).

6. The femur endoprosthesis according to claim 5, wherein a blind bore (13) having an internal thread (14) is provided in the plug cone (10) of the adapter (2) facing the shell (1) with which an end of the draw-in screw (4), equipped with a corresponding thread section (14'), can be engaged in for arrestation.

7. The femur endoprosthesis according to claim 6, wherein the thread section (14') at the end of the draw-in screw (4) has a different pitch than the thread (7) in the interior of the shell (1).

8. The femur endoprosthesis according to claim 5, wherein outward facing surfaces of the flange (11) of the adapter (2) are covered with an open-meshed three-dimensional spatial lattice structure (16).

9. The femur endoprosthesis according to claim 1, wherein surfaces of the draw plate (3) facing the femur are covered with an open-meshed three-dimensional spatial lattice structure (17).

10. The femur endoprosthesis according to claim 1, wherein the draw plate (3) is equipped with at least one abutment in a form of a peg (18) pointing toward the femur, which essentially forms a same angle α with the draw plate (3) as a main axis of the shell (1) with a main axis of the compression of plate (3).

11. A femur endoprosthesis kit for an artificial hip joint, comprising:

a shell (1) which can be implanted without cement in an upper region of a femur below its greater trochanter, a proximal end (8) of the shell being connectable with an adapter (2) for accommodating an artificial spherical joint part (20), the shell including an exterior which is at least partially covered with an open-meshed three-dimensional spatial lattice structure (9);

a draw plate (3) adapted to be mounted on an opposite side of the femur from the shell; and a draw-in screw (4) which is adapted to be fastened through the draw plate and inserted in an interior of the shell through a through bore (5) in a distal end (6) of the shell such that the draw-in screw can be screwed directly into a thread provided in the shell interior in order to draw the shell into an implantated position during surgery to install the femur endoprosthesis.

* * * * *